United States Patent [19]

Carney et al.

[11] 4,218,441
[45] Aug. 19, 1980

[54] O-DEMETHYLSELDOMYCIN FACTOR 5

[75] Inventors: Ronald E. Carney, Gurnee; Robert L. DeVault; James B. McAlpine, both of Libertyville; Arthur C. Sinclair, Lake Forest, all of Ill.

[73] Assignee: Abbott Laboratories, North Chicago, Ill.

[21] Appl. No.: 25,240

[22] Filed: Mar. 29, 1979

[51] Int. Cl.$^2$ .................. A61K 31/71; C07H 15/22
[52] U.S. Cl. ........................... 424/180; 536/17 R; 536/18
[58] Field of Search ............... 536/17 R; 424/180

[56] References Cited

U.S. PATENT DOCUMENTS

| | | | |
|---|---|---|---|
| 3,939,043 | 2/1976 | Nara et al. | 536/17 |
| 4,002,608 | 1/1977 | Wright et al. | 536/17 |
| 4,045,610 | 8/1977 | Nara et al. | 536/17 |
| 4,124,756 | 11/1978 | Martin et al. | 536/17 |

*Primary Examiner*—Johnnie R. Brown

*Attorney, Agent, or Firm*—Robert L. Niblack; Gildo E. Fato; Joyce R. Niblack

[57] ABSTRACT

A new seldomycin factor 5 derivative is provided, O-demethylseldomycin factor 5. The compound is represented by the formula:

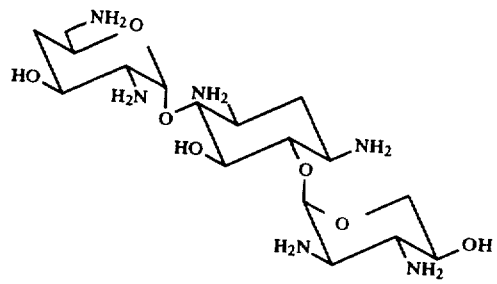

The compound is a potent anti-bacterial agent.

3 Claims, No Drawings

O-DEMETHYLSELDOMYCIN FACTOR 5

Background of the Invention

Seldomycin factor 5 is a broad spectrum antibacterial agent which is produced by the fermentation of *Streptomyces hofunensis* as disclosed in U.S. Pat. No. 3,939,043. The antibiotic is represented by the following structure.

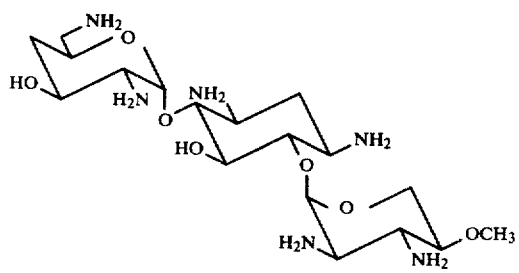

Seldomycin factor 5 is also known as Antibiotic XK-88-5. It is a highly active, broad-spectrum antibiotic effective against both Gram-positive and Gram-negative organisms such as *Staphylococcus aureus, Klebsiella pneumoniae, Escherchia coli* and *Proteus* species. Seldomycin factor 5 is only one of a number of antibiotics produced by the fermentation of *Streptomyces hofunensis*. The isolation and characteristics of seldomycin factor 5 is described in the above referred to U.S. Pat. No. 3,939,043 and the elucidation of its structure is described in the *Journal of Antibiotics* 30 pp 39–49(1977).

Seldomycin factor 5 is an aminoglycoside antibiotic and the aminoglycoside antibiotics are a valuable therapeutic class of antibiotics which includes the kanamycins, streptomycins, gentamicins and fortimicins. While the naturally produced parent antibiotics are valuable, broad spectrum antibiotics, it has been found that chemical modification of the parent structures results in improved entities either by improving the intrinsic activity, improving the activity against resistant strains, or reducing the toxicity. Further, because of the development of aminoglycoside-resistant strains and inactivation of the parent antibiotics by R-mediated factors which can develop, the search for new entities continues which are either improved in one of the above-mentioned ways or in providing reserve antibiotics which have useful activity.

A number of chemical modifications have been made in the seldomycin factor 5 structure. Those modifications have resulted in 3' -epi-seldomycin factor 5, 6' -N-alkyl-seldomycin factor 5 derivatives, 3' -deoxyseldomycin factor 5 and 1-N-acyl-seldomycin factor 5 derivatives among others. The above derivatives are the subject of pending United States patent applications and issued patents. 1-N-alkyl-seldomycin factor 5 derivatives are disclosed in U.S. Pat. No. 4,002,608.

The present invention provides a potent of seldomycin factor 5 derivative 0-demethylseldomycin factor 5.

Summary of the Invention

The present invention provides a new seldomycin factor 5 derivative, 0-demethylseldomycin factor 5. The seldomycin factor 5 derivative of this invention is prepared by treating seldomycin factor 5 with lithium wire in the presence of ethylamine and recovering the 0-demethylseldomycin factor 5 from the reaction mixture. The compound is a potent antibacterial agent.

Detailed Description of Preferred Embodiments

The present invention provides a new seldomycin, 0-demethylseldomycin factor 5 and the pharmaceutically acceptable salts thereof. The compound is represented by the formula

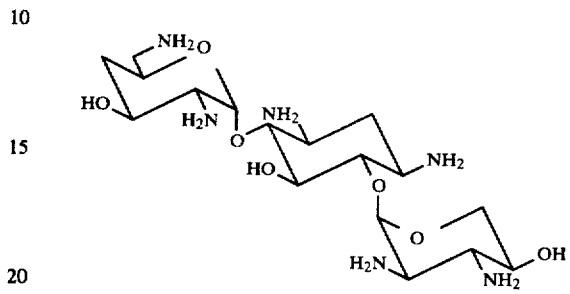

The term "pharmaceutically acceptable salts" refers to the non-toxic acid addition salts of the compounds of this invention which are generally prepared by reacting the free base with a suitable organic or inorganic acid, or can be prepared in situ by methods well known in the art. Such salts include the mono, di, tri, or tetra hydrochloride hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate and like salts.

The compounds of this invention are potent antibacterial agents which are effective against sensitive or susceptible strains of gram-negative and gram-positive bacilli such as *Bacillus subtilus, Staphylococcus aureus, Klebsiella pneumoniae, Proteus vulgaris, Proteus stuartii, Escherichia coli* and *Pseudomonas aeruginosa*. The antibodies of this invention are administered parenterally, i.e. intravenously, intramuscularly, intraperitoneally, or subcutaneously or systemic effect in daily dosages of from 2–10 mg/kg of body weight daily, and preferably from 4–6 mg/kg of body weight daily based on lean body weight as is good medical practice with the aminoglycoside antibiotics. It is further preferred to administer the compounds in divided dosages; i.e. three to four times daily.

The compounds can also be administered orally at the above dosage to sterilize the intestinal tract and can further be administered in suppository form.

The term "susceptible" or "sensitive" strains refers to strains of organisms which have demonstrated to be sensitive to a particular antibiotic in a standard in vitro sensitivity test and thus in vitro activity of an antibiotic against a specific strain of a specific bacillus has been established.

Generally speaking the compound of this invention can be readily prepared by reacting the specific 0-demethylseldomycin factor 5 derivative to be 0-demethylated with eitherlithium wire in the presence of ethylamine, or in the case of the acyl derivatives ($R_3 = $—$COR_4$) with a boron trihalide such as boron tribromide, and recovering the 0-demethylated derivative from the reaction mixture.

The following Example further illustrates the present invention.

EXAMPLE 1

0-Demthylseldomycin factor 5

Seldomycin factor 5(900 mg of free base prepared according to the method of U.S. Pat. No. 3,937,043) is suspended in freshly distilled ethylamine (100 ml) and the mixture is cooled to 0° C. and stirred vigorously as 4 cm of clean ⅛ inch diameter lithium wire is added. After one hour, the mixture is allowed to warm to gentle reflux and after a further 2-½ hours, methanol is added to consume any unreacted lithium. Solvents are removed and the residue is chromatographed over a column (2.2 cm diameter×60 cm) of silica gel. The column is eluted with a mixture of 1 volume of methylene chloride, 2 volumes of ethanol and 1 volume of concentrated ammonium hydroxide. Later fractions are combined and solvent is removed to yield 0-demethylseldomycin factor 5(585 mg).

The carbon magnetic resonance spectrum of 0-demethylseldomycin factor 5 is set forth in table I.

TABLE I

| Carbon Number | Assignment |
| --- | --- |
| 1 | 51.1 |
| 2 | 36.3 |
| 3 | 50.1 |
| 4 | 87.0 |
| 5 | 75.2 |
| 6 | 86.9 |
| 1' | 101.8 |
| 2' | 57.6 |
| 3' | 68.7 |
| 4' | 36.8 |
| 5' | 70.7 |
| 6' | 45.2 |
| 1" | 100.3 |
| 2" | 56.1 |
| 3" | 56.1 |
| 4" | 69.9 |
| 5" | 63.2 |

The above spectrum was determined in deuterium oxide with dioxane as internal reference taken as 67.4 ppm downfield from TMS. Assignments are made from analogy with other know seldomycin factor 5 derivatives and with consideration for the known effects of structural change on carbon magnetic resonance spectra. Interchange of assignments of resonances of similar chemical shift can be made without affecting the characterization of the compounds or the structural inferences of the spectral.

The in vitro antibiotic activity is determined by a two fold dilution test using Streptomycin Assay Agar with yeast extract (at pH 7.9). The inoculum of approximately $1 \times 10^5$ of the indicated test organism is delivered by a multiple inoculator. The minimum inhibitory concentrations for a representative compound, 0-demthylseldomycin factor 5 is set forth in Table II.

The minimum inhibitory concentrations are expressed in micrograms per milliliter.

TABLE II

| Organism | MIC(mcg/ml) |
| --- | --- |
| Bacillus subtilis U. of Ill.10707 | <0.01 |
| Staphylococcus aureus ATCC 6538P | 0.04 |
| Klebsiella pneumoniae ATCC 10031 | 0.04 |
| Proteus vulgaris ATCC 6897 | 0.31 |
| Proteus stuartii ATCC 25825 | 1.25 |
| Eschericha coli ATCC 26 | 0.31 |
| Escherichia coli R3 | >20 |
| Escherichia coli R5 | >20 |
| Escherichia coli R16 | 5 |
| Escherichia coli R19 | 0.16 |
| Escherichia coli 76-2 | 2.5 |
| Escherichia coli NR 79 | 0.31 |
| Pseudomonas aeruginosa BMH#1 | 5 |
| Pseudomonas aeruginosa KY-8512 | 5 |
| Psuedomonas aeruginosa PST | >20 |

The compound of this invention is active as a systemic antibiotic when administered by parenteral routes of administration as discussed hereinabove. It can be administered by the intramuscular, intravenous, intraperitoneal or subcutaneous routes of administration in daily dosages of from 2 to 10 mg/kg based on lean body weight. The compound can also be administered orally to sterilize the intestinal tract and can also be applied topically or administered in suppository form.

Preparations of this invention for parenteral administration include sterile aqueous or non-aqueous solutions, suspensions or emulsions. Examples of suitable non-aqueous solvents or vehicles are propylene glycol, polyethylene glycol, vegetable oils such as olive oil, and injectable organic esters such as ethyl oleate. Such dosage forms may also contain adjuvants such as preserving, wetting, emulsifying and dispersing agents. They may be sterilized by, for example, filtration through a bacteriaretaining filter, by incorporating sterilizing agents into the composition, etc. They can be manufactured in the form of sterile solid compositions which can be dissolved in sterile water, or some other sterile injectable medium immediately before use.

Compositions for rectal administration are preferably suppositories which may contain, in addition to the active substance, excipients such a cocoa buter or a suppository wax.

Solid dosage forms for oral administration include tablets, pills, powders and granules. In such solid dosage forms, the active compound is admixed with at least one inert diluent such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings to ensure the antibiotic reaches the intestinal tract.

Liquid dosage forms for oral administration include pharmaceutically acceptable emulsions, solutions, suspensions, syrups and elixirs containing inert diluents commonly used in the art such as water. Besides such inert diluents, the liquid compositions can also include adjuvants such as wetting agents, emulsifying agents and suspending agents.

We claim:

1. 0-Demethylseldomycin factor 5 or a pharmaceutically acceptable salt thereof.
2. A pharmaceutical composition comprising an antibacterially effective amount of a compound of claim 1 and a pharmaceutically acceptable carrier or diluent.
3. A method of treating infection caused by a susceptible organism comprising administering to an infected patient an antibacterially effective amount of a compound of claim 1.

* * * * *